(12) United States Patent　　　　(10) Patent No.:　US 12,599,741 B2

Thompson et al.　　　　　　　　　　(45) Date of Patent:　　Apr. 14, 2026

(54) SIEVE MODULE

(71) Applicant: Oxus America, Inc., Auburn Hills, MI (US)

(72) Inventors: Loren M. Thompson, Lapeer, MI (US); Andrew Voto, Waterford, MI (US)

(73) Assignee: Oxus America, Inc., Orion Township, MI (US)

( * ) Notice: Subject to any disclaimer, the term of this patent is extended or adjusted under 35 U.S.C. 154(b) by 326 days.

(21) Appl. No.: 18/237,433

(22) Filed: Aug. 24, 2023

(65) Prior Publication Data

US 2024/0066255 A1　　Feb. 29, 2024

Related U.S. Application Data

(60) Provisional application No. 63/401,460, filed on Aug. 26, 2022.

(51) Int. Cl.
| | |
|---|---|
| *A61M 16/10* | (2006.01) |
| *B01D 53/04* | (2006.01) |
| *B01D 53/047* | (2006.01) |

(52) U.S. Cl.
CPC ....... *A61M 16/101* (2014.02); *B01D 53/0407* (2013.01); *B01D 53/0446* (2013.01); (Continued)

(58) Field of Classification Search
CPC ............. A61M 16/001; B01D 53/0407; B01D 53/0446; B01D 53/047; B01D 2253/108; (Continued)

(56) References Cited

U.S. PATENT DOCUMENTS

| | | | | |
|---|---|---|---|---|
| 4,687,573 | A | * | 8/1987 | Miller .................... B01D 15/00 |
| | | | | 210/143 |
| 7,144,446 | B1 | * | 12/2006 | Lessi ................... C01B 13/0259 |
| | | | | 96/108 |

(Continued)

FOREIGN PATENT DOCUMENTS

| | | |
|---|---|---|
| WO | 2021177893 A1 | 9/2021 |
| WO | 2021191824 A1 | 9/2021 |

OTHER PUBLICATIONS

European Search Report for European Patent Application No. EP 23193328.4 dated Feb. 6, 2024, 11 pages.

*Primary Examiner* — Charles G Freay

(74) *Attorney, Agent, or Firm* — Young Basile Hanlon & MacFarlane, P.C.

(57)　　　　　　ABSTRACT

A sieve module includes an impermeable housing, an interface assembly, and an adsorptive material. The interface assembly is connected to a first end of the impermeable housing and includes an inlet port and an outlet port. The inlet port is in fluid communication with a first interior space of the impermeable housing, wherein the inlet port is configured to receive gas from an exterior of the impermeable housing. The outlet port is in fluid communication with a second interior space of the impermeable housing, wherein the outlet port is configured to expel the gas to the exterior of the impermeable housing. An adsorptive material is disposed within the first interior space of the impermeable housing, wherein the interface assembly is configured such that the gas travels from the inlet port to the outlet port by traveling through the adsorptive material.

20 Claims, 6 Drawing Sheets

(52) U.S. Cl.
  CPC ...... *B01D 53/047* (2013.01); *B01D 2253/108*
    (2013.01); *B01D 2256/12* (2013.01); *B01D*
    *2257/102* (2013.01); *B01D 2259/4533*
    (2013.01)

(58) Field of Classification Search
  CPC .......... B01D 2256/12; B01D 2257/102; B01D
    2259/4533
  See application file for complete search history.

(56)                References Cited

U.S. PATENT DOCUMENTS

| | | | |
|---|---|---|---|
| 8,388,745 | B1 | 3/2013 | Pelletier et al. |
| 9,993,765 | B2 | 6/2018 | Galbraith et al. |
| 10,252,212 | B2 * | 4/2019 | Byrd .................. B01D 53/0415 |
| 10,786,644 | B2 | 9/2020 | Taylor et al. |
| 2012/0266883 | A1 * | 10/2012 | Taylor .............. A61M 16/0677 |
| | | | 128/205.12 |
| 2017/0348501 | A1 | 12/2017 | Taylor et al. |
| 2020/0324070 | A1 | 10/2020 | Taylor et al. |
| 2021/0154427 | A1 | 5/2021 | Poon et al. |

* cited by examiner

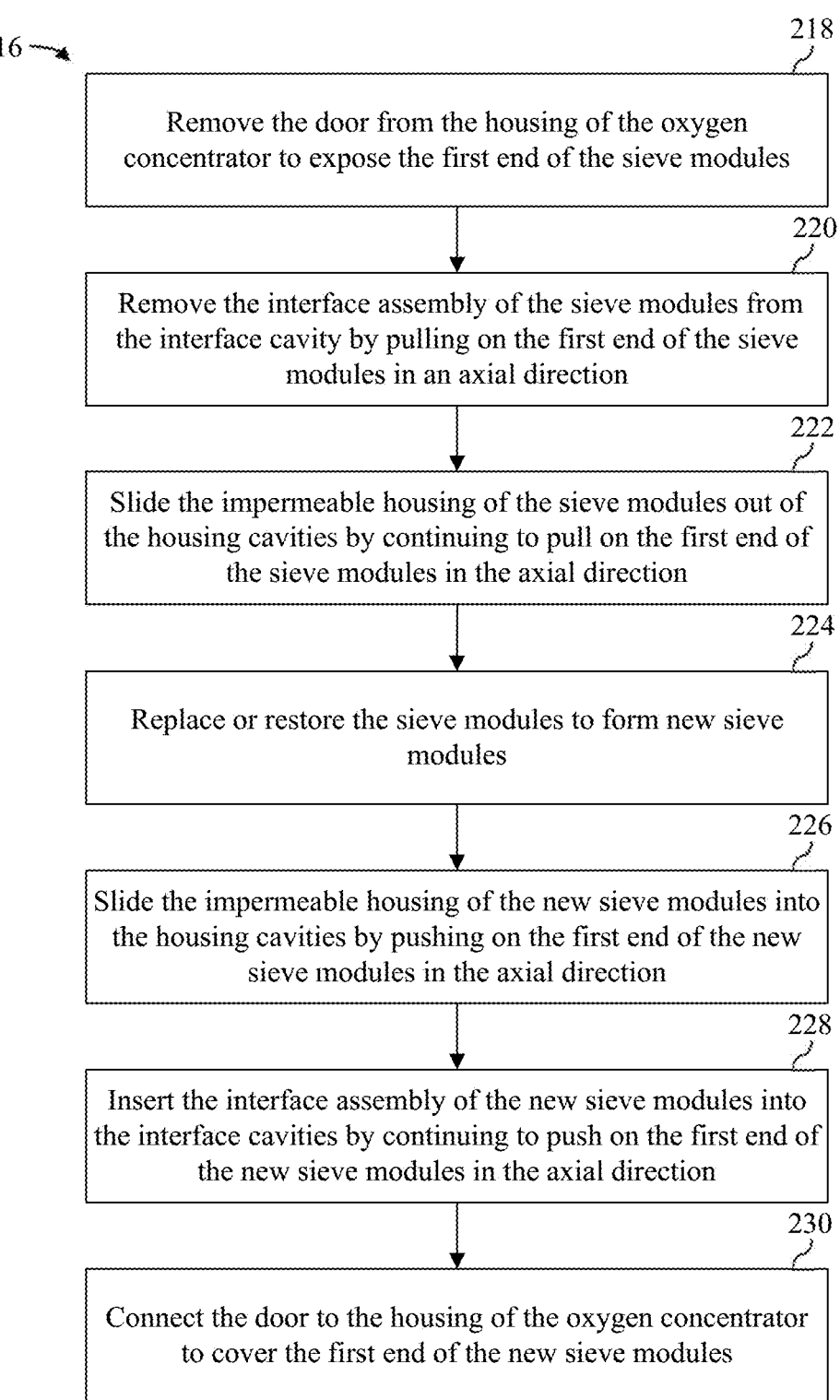

216

218

Remove the door from the housing of the oxygen concentrator to expose the first end of the sieve modules

220

Remove the interface assembly of the sieve modules from the interface cavity by pulling on the first end of the sieve modules in an axial direction

222

Slide the impermeable housing of the sieve modules out of the housing cavities by continuing to pull on the first end of the sieve modules in the axial direction

224

Replace or restore the sieve modules to form new sieve modules

226

Slide the impermeable housing of the new sieve modules into the housing cavities by pushing on the first end of the new sieve modules in the axial direction

228

Insert the interface assembly of the new sieve modules into the interface cavities by continuing to push on the first end of the new sieve modules in the axial direction

230

Connect the door to the housing of the oxygen concentrator to cover the first end of the new sieve modules

FIG. 6

SIEVE MODULE

CROSS-REFERENCE TO RELATED APPLICATION(S)

This application claims the benefit of, and priority to, U.S. Provisional Application No. 63/401,460, filed on Aug. 26, 2022, the content of which is hereby incorporated by reference in its entirety herein for all purposes.

TECHNICAL FIELD

The present disclosure relates generally to sieve modules for oxygen concentrators.

BACKGROUND

Oxygen concentrator systems generate substantially pure (e.g., 82-96% pure) oxygen gas using ambient air as an input gas. Oxygen concentrator systems are commonly used for medical applications by patients who have a need for substantially pure oxygen. Oxygen concentrator systems include portable systems that can be carried by patients, and non-portable systems that are often used in a medical facility or in a residential setting.

Some known oxygen concentrator systems operate on a pressure swing adsorption or vacuum pressure swing adsorption cycle. In such systems, ambient air is pressurized in a sieve module that includes a bed of an adsorptive material that adsorbs nitrogen (e.g., zeolite), and substantially pure oxygen is then released from the sieve module while the nitrogen is retained by the adsorptive material. The nitrogen may then be purged from the adsorptive material.

SUMMARY

Disclosed herein are embodiments of sieve modules for oxygen concentrators, interface assemblies of sieve modules for oxygen concentrators, and methods for using the sieve modules with oxygen concentrators.

An aspect of the disclosure is a sieve module. The sieve module includes an impermeable housing including a first end, a second end opposite the first end, and a diffuser positioned at the second end that defines a first interior space and a second interior space within the impermeable housing. The first interior space and the second interior space are in fluid communication solely at the second end of the impermeable housing. The sieve module also includes an interface assembly connected to the first end of the impermeable housing. The interface assembly includes an inlet port in fluid communication with the first interior space of the impermeable housing, wherein the inlet port is configured to receive gas from an exterior of the impermeable housing, and an outlet port in fluid communication with the second interior space of the impermeable housing, wherein the outlet port is configured to expel the gas to the exterior of the impermeable housing. The sieve module also includes an adsorptive material that is disposed within the first interior space of the impermeable housing, wherein the interface assembly is configured such that the gas travels from the inlet port to the outlet port by traveling through the adsorptive material.

In some implementations of the sieve module, the interface assembly includes a spacing portion pneumatically connected to the first end of the impermeable housing and extending perpendicular to a housing axis of the impermeable housing in a direction away from the impermeable housing, wherein the housing axis extends through the first end and the second end of the impermeable housing. The interface assembly also includes an axial portion pneumatically connected to the spacing portion and extending parallel to the housing axis in a direction generally toward the second end of the impermeable housing.

The inlet port and the outlet port may both be disposed on the axial portion of the interface assembly. In some implementations, the interface assembly further comprises a gasket disposed within the spacing portion of the interface assembly, wherein the gasket defines an inlet channel that pneumatically connects the inlet port to the first interior space of the impermeable housing and an outlet channel that pneumatically connects the outlet port to the second interior space of the impermeable housing.

In some implementations, the interface assembly further comprises a first seal disposed along the axial portion, and a second seal disposed along the axial portion and spaced apart from the first seal, wherein the inlet port is disposed between the first seal and the second seal, and the outlet port is disposed at an end of the axial portion that is distal from the spacing portion. In some implementations, the first seal and the second seal extend circumferentially around the axial portion of the interface assembly.

In some implementations, the outlet port is disposed at an end of the axial portion that is distal from the spacing portion, and the inlet port extends through a side wall of the axial portion. In some implementations, the outlet port has an orientation that is in alignment with a housing axis of the impermeable housing and the inlet port has an orientation that is substantially perpendicular to the outlet port.

In some implementations, the adsorptive material is configured to filter nitrogen from the gas traveling through the adsorptive material. In some implementations, the adsorptive material comprises zeolite.

An aspect of the disclosure is an interface assembly for a sieve module. The interface assembly includes a spacing portion configured to be connected to an impermeable housing of the sieve module such that the spacing portion extends away from a housing axis of the impermeable housing. The interface assembly also includes an axial portion that is connected to the spacing portion, is configured to be located radially outward from the impermeable housing, and extends away from the spacing portion of the interface assembly in a direction parallel to the housing axis of the impermeable housing. The interface assembly also includes an inlet port positioned on the axial portion and an outlet port positioned on the axial portion.

In some implementations of the interface assembly, the spacing portion is configured to be connected to the impermeable housing at a first end of the impermeable housing, and the axial portion is configured to extend from the spacing portion toward a second end of the impermeable housing.

In some implementations of the interface assembly, the outlet port is disposed at an end of the axial portion that is distal from the spacing portion, and the inlet port extends through a side wall of the axial portion. In some implementations of the interface assembly, the outlet port has an orientation that is in alignment with a housing axis of the impermeable housing and the inlet port has an orientation that is substantially perpendicular to the outlet port.

In some implementations of the interface assembly, the interface assembly includes an inlet channel extending from the inlet port through the axial portion and the spacing portion for fluid communication with the impermeable housing and an outlet channel extending from the outlet port through the axial portion and the spacing portion for fluid communication with the impermeable housing.

In some implementations of the interface assembly, the interface assembly includes a gasket disposed within the spacing portion and configured to separate the inlet channel from the outlet channel in the spacing portion. In some implementations of the interface assembly, the axial portion includes a divider wall to separate the inlet channel from the outlet channel in the axial portion.

An aspect of the disclosure is an interface assembly for a sieve module. The interface assembly includes a first interface part and a second interface part that is connected to the first interface part. The interface assembly also includes a gasket disposed between the first interface part and the second interface part to define at least part of an inlet channel and an outlet channel, wherein the inlet channel and the outlet channel are separated by the gasket.

In some implementations of the interface assembly, the first interface part and the second interface part cooperate to define a spacing portion that is configured to extend away from a housing axis of an impermeable housing of the sieve module. The first interface part also defines an axial portion that is connected to the spacing portion, is configured to be located radially outward from the impermeable housing, and extends away from the spacing portion of the interface assembly in a direction parallel to the housing axis of the impermeable housing.

In some implementations of the interface assembly, an inlet port is positioned on the axial portion and is in communication with the inlet channel. In some implementations of the interface assembly, an outlet port is positioned on the axial portion and is in communication with the outlet channel.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 6 is a flowchart that shows a process for replacing sieve modules inserted into the oxygen concentrator.

DETAILED DESCRIPTION

The disclosure herein relates to sieve modules that, when inserted into an oxygen concentrator, operate to remove nitrogen from ambient air to produce substantially pure (e.g., 82-96% pure) oxygen. Sieve modules may require servicing or replacing, whereby the sieve modules are disconnected and removed from the oxygen concentrator.

Known sieve modules may require an operator to perform multiple actions and/or access multiple locations about the sieve modules and/or oxygen concentrator to disconnect and remove the sieve modules from the oxygen concentrator. What may be desired are an oxygen concentrator and sieve modules that enable an operator to disconnect and remove the sieve modules from the oxygen concentrator with fewer actions and by accessing only one end of the sieve module.

Figure 1:
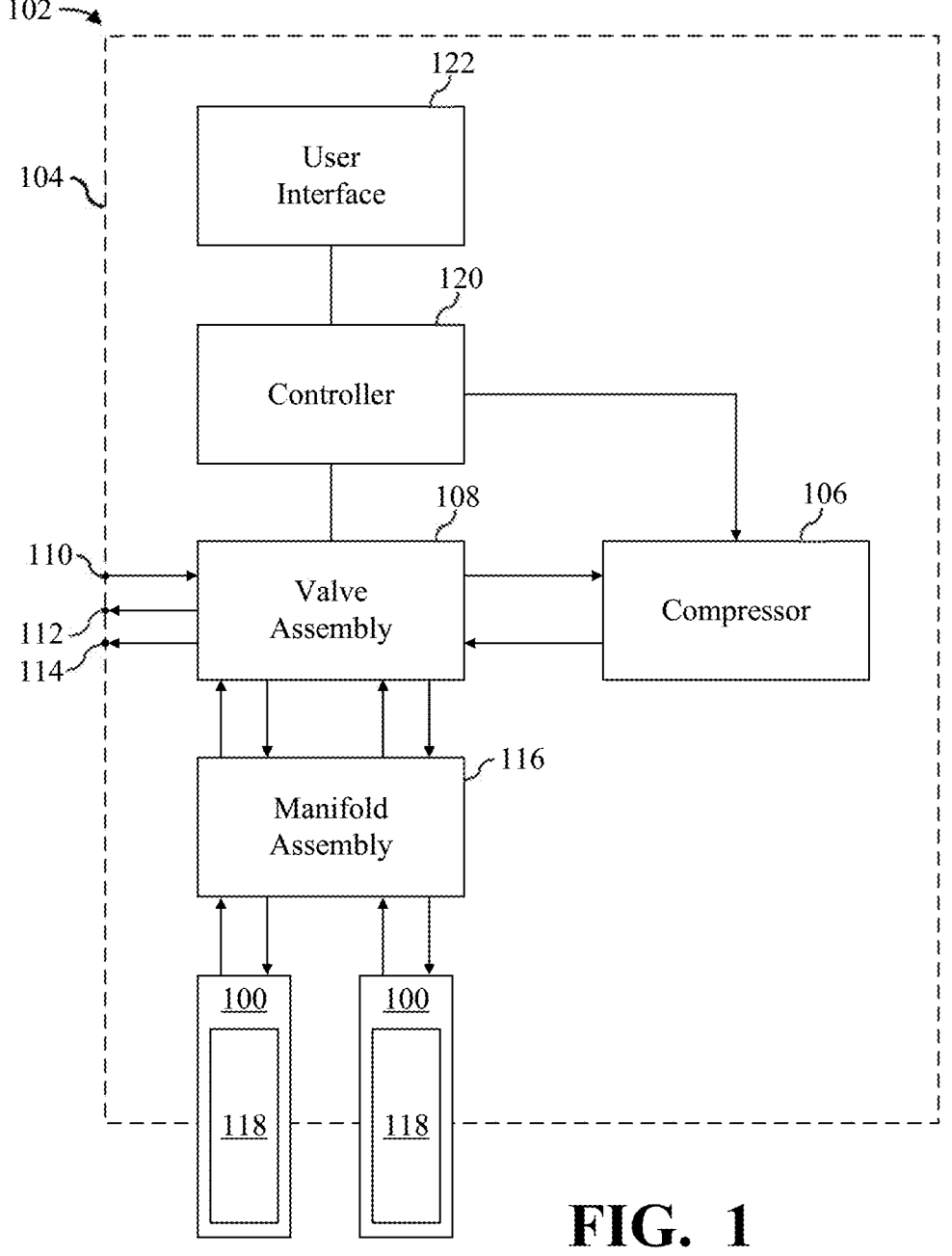
FIG. 1 is a block diagram showing an oxygen concentrator and two sieve modules in accordance with the present disclosure.

FIG. 1 is a block diagram showing an oxygen concentrator 102 and two sieve modules 100. The oxygen concentrator 102 may operate on a pressure swing adsorption (PSA) cycle or a vacuum pressure swing adsorption (VPSA) cycle as are well known in the art. The description herein refers to the PSA cycle as an example, but is also applicable to oxygen concentration according to the VPSA cycle. The oxygen concentrator 102 may be a portable system that can be carried by a user, or may be a non-portable system that is used in a medical facility or in a residential setting. The sieve modules 100 and the oxygen concentrator 102 are cooperatively operable to receive air as an input gas and separate the air into constituent components. In particular, the sieve modules 100 and the oxygen concentrator 102 may be cooperatively operable to filter nitrogen from the input gas to generate a product gas that is substantially pure oxygen. The substantially pure oxygen has a much higher oxygen concentration than ambient air. As an example, the substantially pure oxygen may be approximately 82-96% oxygen.

To implement the PSA cycle, the oxygen concentrator 102 may include a housing 104, a compressor 106, and valve assembly 108. The housing 104 may be configured to contain the compressor 106 and the valve assembly 108 therein. The housing 104 may also be configured to receive the sieve modules 100. Furthermore, the compressor 106 may be pneumatically connected to the valve assembly 108 to facilitate the transfer of pressurized gas across the valve assembly 108 and throughout the oxygen concentrator 102 and sieve modules 100.

The oxygen concentrator 102 may further include an ambient air inlet 110, a waste gas outlet 112, a product gas outlet 114, and a manifold assembly 116 that are in fluid communication with the valve assembly 108. The sieve modules 100 may be in fluid communication with the manifold assembly 116 when the sieve modules 100 are inserted into the housing 104. The ambient air inlet 110 may be exposed to ambient air from the environment around the oxygen concentrator 102. The product gas outlet 114 may be configured to deliver the product gas for use in an intended application, such as by supplying the product gas to a cannula for administration to a person. The waste gas outlet 112 may be configured to expel waste gas produced during the PSA cycle, such as by expelling the waste gas to the environment around the oxygen concentrator 102.

During the PSA cycle, the sieve modules 100 may undergo at least two phases, including an adsorption phase in which the product gas is produced, and a purge phase in which waste gas is purged. In embodiments including two of the sieve modules 100, during the PSA cycle, one of the sieve modules 100 may undergo the adsorption phase while the other one of the sieve modules 100 undergoes the purge phase. To produce the product gas (e.g., substantially pure oxygen), during the adsorption phase, air from the ambient air inlet 110 is supplied to the compressor 106 by operation of the valve assembly 108. The air is then supplied to one of the sieve modules 100 at a pressure that is higher than ambient pressure. The air is subsequently released from the one of the sieve modules 100 as the product gas. In particular, after the one of the sieve modules 100 is pressurized, the valve assembly 108 is operated to establish fluid communication between the one of the sieve modules 100 and the product gas outlet 114 to supply the product gas to the product gas outlet 114 for use. After a certain amount of the product gas has been produced, the one of the sieve modules 100 may transition from the adsorption phase to the purge phase, and the other one of the sieve modules 100 may transition from the purge phase to the adsorption phase where the above-described process is repeated by the other one of the sieve modules 100.

The sieve modules 100 may include an adsorptive material 118 that is used to separate oxygen from other components of ambient air, such as nitrogen. In some embodiments, the adsorptive material 118 may be a zeolite material. The pressure at which the air is supplied to the sieve modules 100 during the adsorption phase is selected based on the material properties of the adsorptive material 118. In particular, adsorption is dependent on pressure, and the volume of a gas that is adsorbed by the adsorptive material 118 increases as the pressure increases. In addition, nitrogen is adsorbed by the adsorptive material 118 that is used in the sieve modules 100 (e.g., zeolite) more readily than oxygen is at the same pressure. Thus, pressurization of the sieve modules 100 causes adsorption of a portion of the nitrogen in the air supplied to the sieve modules 100. During the purge phase, the sieve modules 100 may be purged by lowering the pressure in the sieve modules 100 so that the nitrogen is released from the adsorptive material 118 as the waste gas. The waste gas may then be vented out of the waste gas outlet 112 of the oxygen concentrator 102. In particular, the valve assembly 108 may be operated to establish fluid communication between the sieve modules 100 and the waste gas outlet 112 to expel the waste gas out of the waste gas outlet 112.

The oxygen concentrator 102 may further include a controller 120 and a user interface 122. The controller 120 is configured to regulate operation of the oxygen concentrator 102 and control operation of various components of the oxygen concentrator 102 (e.g., the compressor 106, the valve assembly 108, and/or other components). In some embodiments, the controller 120 may include a general-purpose computing device, such as a computing device that includes one or more processors, a short term memory device, and a long term storage device. In some embodiments, the controller 120 may include a special purpose computing device, such as an integrated circuit or an application specific integrated circuit. The controller 120 may be provided with control software that is executed by the controller 120 to cause the controller 120 to cause operation of the various components of the oxygen concentrator 102 in the desired manner. The user interface 122 may include components such as buttons, knobs, and other types of input components that allow a user to change the operating state of the oxygen concentrator 102, such as by starting and stopping production of the product gas. The user interface 122 may include output components that show information regarding the system of the oxygen concentrator 102.

Figure 2:
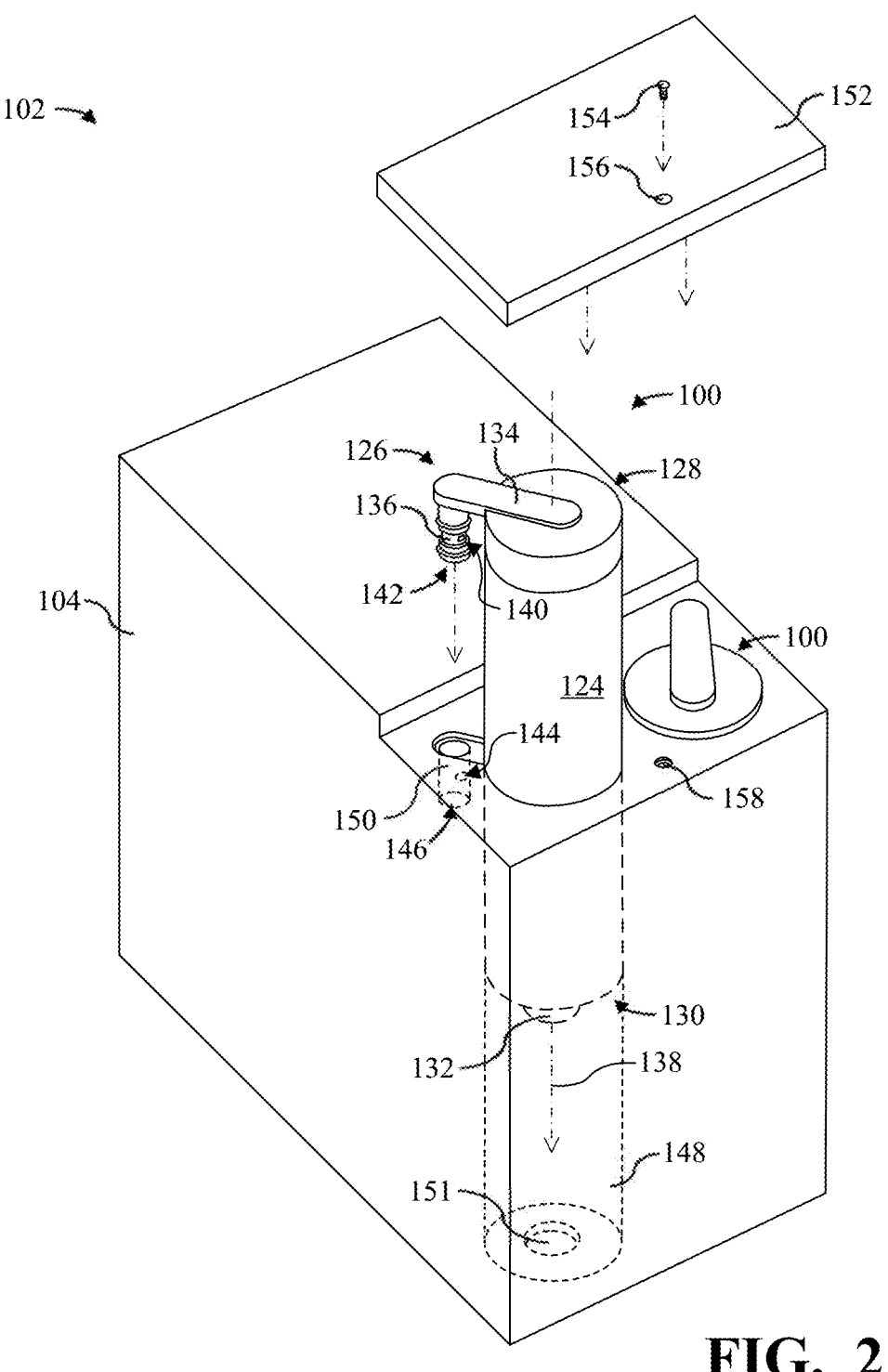
FIG. 2 is a perspective view illustration of the oxygen concentrator showing one of the sieve modules in a partially inserted position and showing another one of the sieve modules in a fully inserted position.

FIG. 2 is a perspective view illustration showing the oxygen concentrator 102 and two of the sieve modules 100, wherein one of the sieve modules 100 is shown in a partially inserted position and the other one of the sieve modules 100 is shown in a fully inserted position. In some embodiments, the sieve modules 100 may each include an impermeable housing 124 and an interface assembly 126. The impermeable housing 124 may be configured to contain the adsorptive material 118 therein. The interface assembly 126 may be configured to facilitate fluid communication between the impermeable housing 124 and the oxygen concentrator 102.

In some embodiments, the impermeable housing 124 may have a geometry that is substantially cylindrical (as shown in FIG. 2) in order to resist deformation (i.e., elastic or plastic deformation) resulting from repeated pressurization of the sieve modules 100 that occurs during the PSA cycle. In other embodiments, the impermeable housing 124 may have some other elongated geometry that is resilient against pressurization induced deformation. As an example, the impermeable housing 124 may be an elongated cuboid with rounded edges. The impermeable housing 124 may be comprised of any generally rigid material that is suitable to resist the deformation forces associated with the PSA cycle and that is substantially impermeable to gas (e.g., oxygen and nitrogen). For example, the impermeable housing 124 may be comprised of steel, aluminum, titanium, fiber-reinforced polymer, or any other substantially impermeable material that is resilient to repeated pressurization cycles.

In some embodiments, the impermeable housing 124 may include a first end 128 and a second end 130 opposite the first end 128. In such embodiments, the interface assembly 126 may be connected to the first end 128. Furthermore, the impermeable housing 124 may include an alignment feature 132 located at the second end 130 of the impermeable housing 124. The alignment feature 132 may be operable to facilitate alignment of the sieve module 100 with the housing 104 of the oxygen concentrator 102 when the sieve module 100 is inserted into the housing 104.

The interface assembly 126 may include a spacing portion 134 and an axial portion 136. The spacing portion 134 may be connected to the first end 128 of the impermeable housing 124 and may extend away from the impermeable housing 124. The axial portion 136 may be connected to the spacing portion 134 and may extend away from the spacing portion 134 in a direction generally toward the second end 130 of the impermeable housing 124. In some embodiments, the spacing portion 134 may extend away from the impermeable housing 124 in a direction perpendicular to a housing axis 138 that extends axially along the impermeable housing 124 through the first end 128 and the second end 130. In other embodiments, the spacing portion 134 may extend away from the impermeable housing 124 at some other angle relative to the housing axis 138 (e.g., forty-five degrees, sixty-seven degrees, or some other angle). The axial portion 136 may be located outward (e.g., radially outward) from the impermeable housing 124 and may extend away from the spacing portion 134 of the interface assembly 126 in a direction parallel to the housing axis 138.

The axial portion 136 may have any substantially elongated geometry. In the illustrated implementation, the axial portion 136 has a geometry that is substantially cylindrical and includes a recessed portion extending circumferentially around the axial portion 136. In other embodiments, the axial portion 136 may be substantially cylindrical but not include such a recessed portion. In other embodiments, the axial portion 136 may have some other substantially elongated geometry. For example, the axial portion 136 may have a geometry that resembles an elongated cuboid, a triangular prism, or some other shape.

The interface assembly 126 includes an inlet port 140 and an outlet port 142 that are located on the axial portion 136 of the interface assembly 126. The inlet port 140 and the outlet port 142 are configured to form a pneumatic connection with the oxygen concentrator 102. In the illustrated implementation, the inlet port 140 and the outlet port 142 are configured to form a pneumatic connection with the manifold assembly 116 when the sieve module 100 is in the fully inserted position. In some embodiments, the manifold assembly 116 may include a manifold inlet 144 and a manifold outlet 146 that are configured to facilitate fluid communications with the inlet port 140 and the outlet port 142, respectively. The inlet port 140 may be operable to receive pressurized air from the manifold inlet 144 to be transferred to the adsorptive material 118 during the adsorption phase of the PSA cycle. Furthermore, the inlet port 140 may be operable to transfer the waste gas from within the impermeable housing 124 to the manifold inlet 144 to be expelled out of the waste gas outlet 112 during the purge phase of the PSA cycle. The outlet port 142 may be configured to transfer product gas from within the impermeable housing 124 to the manifold outlet 146 to be expelled out of the product gas outlet 114 for use in an intended application.

In some embodiments, the housing 104 of the oxygen concentrator 102 may define one or more housing cavities 148 and one or more interface cavities 150 that are configured to receive the impermeable housing 124 and the interface assembly 126 of the sieve modules 100. Particularly, the interface cavities 150 may be configured to receive the axial portion 136 of the interface assembly 126. In some embodiments, one of each of the housing cavities 148 and the interface cavities 150 may be provided for each of the sieve modules 100 (as shown in FIG. 2). In such embodiments, a number of the sieve modules 100 may correspond to a number of the housing cavities 148 and/or the interface cavities 150. In other embodiments, a single one of the housing cavities 148 and/or the interface cavities 150 may be provided for multiple of the sieve modules 100. In such embodiments, for example, the impermeable housing 124 of multiple of the sieve modules 100 may be received by a single one of the housing cavities 148. As another example, the interface assembly 126 of multiple of the sieve modules 100 may be received by a single one of the interface cavities 150.

The housing cavities 148 may have any geometry that facilitates a mating engagement with the impermeable housing 124. For example, where the impermeable housing 124 has a geometry that is substantially cylindrical, the housing cavities 148 may also have a geometry that is substantially cylindrical to be complementary to the impermeable housing 124. The term "complementary" as used herein refers to a geometry (e.g., the geometry of the impermeable housing 124) that may be received by another geometry (e.g., the geometry of the housing cavities 148), such that the geometries engage each other to define a desired position of the geometries relative to each other. The relative position of the geometries may deviate slightly as a result of variations in the geometries resulting from manufacturing tolerances, deviations, or the like.

In embodiments where the impermeable housing 124 of each of the sieve modules 100 includes the alignment feature 132, the housing cavities 148 may include a corresponding alignment feature 151. In such an embodiment, the corresponding alignment feature 151 may have a geometry that is complementary to the alignment feature 132 of the impermeable housing 124.

Furthermore, the housing cavities 148 may be configured to conceal the impermeable housing 124 from the environment around the oxygen concentrator 102 when the sieve modules 100 are in the fully inserted position (as shown in FIG. 2). Alternatively, the housing cavities 148 may be configured to expose portions of the impermeable housing 124 to the environment around the oxygen concentrator 102 when the sieve modules 100 are in the fully inserted position. In embodiments where the housing cavities 148 are configured to conceal the impermeable housing 124 from the environment around the oxygen concentrator 102, for example, the housing cavities 148 may extend around sides of the impermeable housing 124 and around the second end 130 of the impermeable housing 124. In such an embodiment, however, the first end 128 may remain exposed to the environment around the oxygen concentrator 102 to enable the sieve modules 100 to be inserted into and/or removed from the housing cavities 148. In embodiments where the housing cavities 148 are configured to expose portions of the impermeable housing 124 to the environment around the oxygen concentrator 102, for example, the housing cavities 148 may include a cup that extends around the second end 130 of the impermeable housing 124, and may further include a collar that extends circumferentially around the first end 128 of the impermeable housing 124. In such an embodiment, the sides of the impermeable housing 124 may remain exposed to the environment around the oxygen concentrator 102 when the sieve modules 100 are in the fully inserted position.

The interface cavities 150 may have any geometry that facilitates a mating engagement with the interface assembly 126 (e.g., the axial portion 136 of the interface assembly 126) of the sieve modules 100. For example, where the axial portion 136 of the interface assembly 126 has a geometry that is substantially cylindrical, the interface cavities 150 may also have a geometry that is substantially cylindrical to be complementary to the axial portion 136 of the interface assembly 126 (as shown in FIG. 2). The impermeable housing 124 and the axial portion 136 of the interface assembly 126 both being aligned parallel with the housing axis 138 enables the sieve modules 100 to slide in and out of the housing cavities 148 and the interface cavities 150 by pulling or pushing on the first end 128 of the impermeable housing 124 in an axial direction parallel to the housing axis 138.

In some embodiments, the manifold assembly 116 may define the interface cavities 150 rather than the housing 104 of the oxygen concentrator 102. In such embodiments, the housing 104 of the oxygen concentrator 102 may include an aperture positioned adjacent to the interface cavities 150 to allow the interface assembly 126 to be inserted into the interface cavities 150. Furthermore, in some embodiments, the manifold assembly 116 and the housing 104 of the oxygen concentrator 102 may cooperatively define the interface cavities 150. In such an embodiment, the housing 104 may define some portions of the geometry of the interface cavities 150 and the manifold assembly 116 may define other portions of the geometry of the interface cavities 150.

In some embodiments, the oxygen concentrator 102 may include a door 152 configured to secure the sieve modules 100 to the housing 104 of the oxygen concentrator 102 when the sieve modules 100 are in the fully inserted position. When the sieve modules 100 are in the fully inserted position, the door 152 may be removably connected to the housing 104 adjacent to the first end 128 of the impermeable housing 124 to prevent the sieve module 100 from becoming removed from the housing 104 of the oxygen concentrator 102. The door 152 may be removably connected to the housing 104 by any conventional means, such as, for example, with a threaded fastener 154, clips, snaps, magnets, or the like. In embodiments where the threaded fastener 154 is employed, the threaded fastener 154 may extend through a door aperture 156 located on the door 152 and into a threaded housing aperture 158 located on the housing 104.

Figure 3:
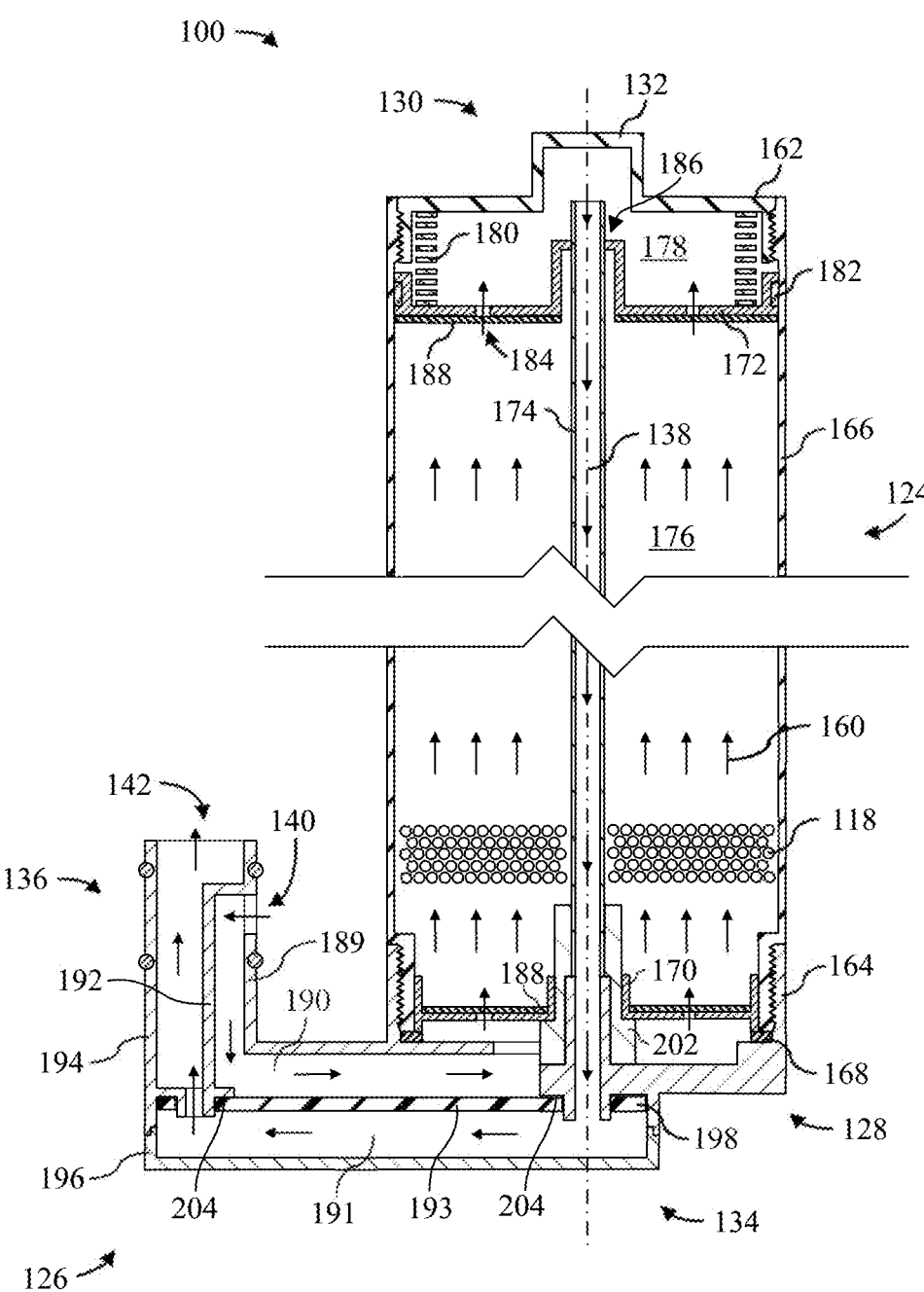
FIG. 3 is a cross-sectional, schematic view illustration of one of the sieve modules.

FIG. 3 shows a cross-sectional, schematic view illustration of one of the sieve modules 100, wherein arrows 160 represent a path in which gas may travel during the adsorption phase of the PSA cycle. During the purge phase of the PSA cycle, gas may travel in a direction that is opposite the direction of the arrows 160. During the adsorption phase of the PSA cycle, pressurized air may be received through the inlet port 140 of the interface assembly 126. The pressurized air may then travel into the impermeable housing 124 where a portion of the pressurized air (e.g., nitrogen) may be removed from the air by the adsorptive material 118 to form the product gas (e.g., substantially pure oxygen). The product gas may then travel out of the impermeable housing 124 to be expelled through the outlet port 142.

The impermeable housing 124 may be comprised of two or more interconnected portions or may be comprised of a unitary body. In embodiments where the impermeable housing 124 is comprised of two or more interconnected portions, the impermeable housing 124 may, for example, include a cap portion 162 positioned at the second end 130 of the impermeable housing 124, a base portion 164 positioned at the first end 128 of the impermeable housing 124, and a middle portion 166 positioned between the cap portion 162 and the base portion 164 (as shown in FIG. 3). In such an embodiment, the two or more portions may be connected in any sealed manner such as to prevent gas from escaping from within the impermeable housing 124 to an exterior of the impermeable housing 124. For example, the cap portion 162 and the base portion 164 may each threadedly engage with the middle portion 166. Furthermore, a first end seal 168 may be positioned at an interface between the base portion 164 and the middle portion 166, and a second end seal (not pictured) may be positioned at an interface between the middle portion 166 and the cap portion 162.

In some embodiments, the sieve module 100 may further include a first end diffuser 170 positioned at the first end 128 of the impermeable housing 124, a second end diffuser 172 positioned at the second end 130 of the impermeable housing 124, and a transfer tube 174 extending between the first end 128 and the second end 130 of the impermeable housing 124. Furthermore, a first interior space 176 and a second interior space 178 may be defined within the impermeable housing 124. The first interior space 176 may be defined between the middle portion 166 of the impermeable housing 124 and the transfer tube 174, and between the first end diffuser 170 and the second end diffuser 172. The first interior space 176 may be configured to contain the adsorptive material 118 therein. Although the adsorptive material 118 is depicted in FIG. 3 as filling only a portion of a volume of the first interior space 176, the adsorptive material 118 is only depicted in this way for clarity purposes, and a person having ordinary skill in the art will understand that the adsorptive material 118 may substantially fill an entirety of the volume of the first interior space 176. The second interior space 178 may be defined between the cap portion 162 of the impermeable housing 124 and the second end diffuser 172. In some embodiments, the first interior space 176 and the second interior space 178 may be in fluid communication solely through the second end diffuser 172 located at the second end 130 of the impermeable housing 124. The transfer tube 174 may be operable to facilitate fluid communication between the second interior space 178 and the outlet port 142 of the interface assembly 126.

To facilitate containment of the adsorptive material 118 within the first interior space 176, a spring 180 may be positioned between the second end diffuser 172 and the cap portion 162 of the impermeable housing 124 such that a force is exerted by the spring 180 onto the second end diffuser 172. Furthermore, the second end diffuser 172 may slidingly engage with the middle portion 166 of the impermeable housing 124 such that the spring 180 may cause a compressive force to be exerted upon the adsorptive material 118 by the second end diffuser 172. Additionally, a diffuser seal 182 may be positioned at an interface between the second end diffuser 172 and the middle portion 166 of the impermeable housing 124 such that the adsorptive material 118 may not escape from the first interior space 176 into the second interior space 178.

The first end diffuser 170 and the second end diffuser 172 may include a plurality of diffuser apertures 184 that are positioned in a spaced relationship along a surface of the first end diffuser 170 and the second end diffuser 172. For example, the diffuser apertures 184 may be positioned equidistant to each other and extend around a central aperture 186 that the transfer tube 174 extends through. During the adsorption phase of the PSA cycle, the diffuser apertures 184 of the first end diffuser 170 may be operable to diffuse pressurized air through the adsorptive material, whereby the product gas may travel through the diffuser apertures 184 of the second end diffuser 172 to be expelled out of the outlet port 142. During the purge phase of the PSA cycle, the diffuser apertures 184 of the second end diffuser 172 may be operable to diffuse gas through the adsorptive material 118, whereby the waste gas may travel through the diffuser apertures 184 of the first end diffuser 170 to be expelled out of the inlet port 140. Furthermore, in some embodiments, diffuser membranes 188 may be positioned adjacent to the first end diffuser 170 and the second end diffuser 172 to further facilitate diffusion of gas throughout the adsorptive material 118.

Figure 4:
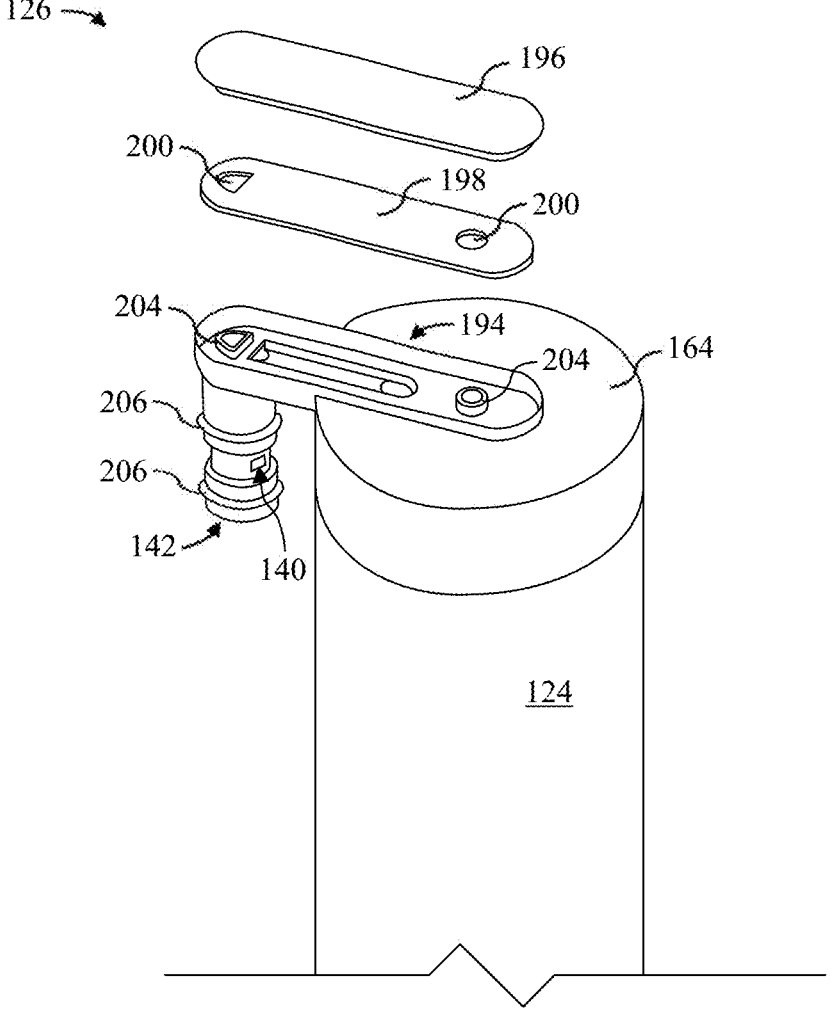
FIG. 4 is a perspective, exploded view illustration showing an interface assembly of one of the sieve modules.

Referring to FIGS. 3 and 4, the interface assembly 126 may be connected to the base portion 164 of the impermeable housing 124 or may be formed integrally with the base portion 164 (as shown in FIGS. 3 and 4). In the illustrated implementation, the outlet port 142 is positioned on the axial portion 136 such that the outlet port 142 forms an opening at an end of the axial portion 136 that is opposite an end of the axial portion 136 that is connected to the spacing portion 134. Furthermore, the inlet port 140 is positioned on the axial portion 136 such that the inlet port 140 extends through a side wall 189 of the axial portion 136. In other embodiments, the outlet port 142 may extend through the side wall 189 of the axial portion 136 and the inlet port 140 may form an opening at the end of the axial portion 136 that is opposite the end of the axial portion 136 that is connected to the spacing portion 134. In other embodiments, both the inlet port 140 and the outlet port 142 may extend through the side wall 189 of the axial portion 136.

In embodiments where the inlet port 140 and/or the outlet port 142 extends through the side wall 189 of the axial portion 136, the inlet port 140 and/or the outlet port 142 may be positioned at any location along the side wall 189. For example, where the outlet port 142 forms an opening at the end of the axial portion 136 and the inlet port 140 extends through the side wall 189 of the axial portion 136, the inlet port 140 may be centered between the end of the axial portion 136 that includes the outlet port 142 and the end of the axial portion 136 that is connected to the spacing portion 134 in the longitudinal direction. Alternatively, the inlet port 140 may not be centered between the end of the axial portion 136 that includes the outlet port 142 and the end of the axial portion 136 that is connected to the spacing portion 134 in the longitudinal direction, and instead may be positioned at some other location along the side wall 189 of the axial portion 136 (i.e., may be positioned proximal the end of the axial portion 136 that includes the outlet port 142, or proximal the end of the axial portion 136 that is connected to the spacing portion 134, relative to a center between the ends of the axial portion 136).

Furthermore, although the inlet port 140 is shown to be aligned with a plane that bisects the impermeable housing 124 and the interface assembly 126 (i.e., a plane that extends longitudinally along the spacing portion 134 of the interface assembly 126), in some embodiments the inlet port 140 may be axially rotated about the axial portion 136 of the interface assembly 126 such that the inlet port 140 is not aligned with the plane. For example, the inlet port 140 may be positioned 45 degrees relative to the plane, 90 degrees relative to the plane, 135 degrees relative to the plane, or at some other angle relative to the plane. Positioning the inlet port 140 such that the inlet port 140 is not aligned with the plane may permit additional locations with which components (e.g., the manifold assembly 116, the valve assembly 108, etc.) may be packaged within the housing 104 of the oxygen concentrator 102.

In the illustrated implementation, the outlet port 142 has an orientation that is in alignment with the housing axis 138 and the inlet port 140 has an orientation that is substantially perpendicular to the outlet port 142 (i.e., has an orientation that is perpendicular to the housing axis 138). In other embodiments, the outlet port 142 may not have an orientation that is in alignment with the housing axis 138. Furthermore, the inlet port 140 may have an orientation that is not perpendicular to the outlet port 142, but is rather oriented at some other angle relative to the inlet port 140 (e.g., 75 degrees, 115 degrees, etc.).

The interface assembly 126 may define an inlet channel 190 and an outlet channel 191. The inlet channel 190 may extend through the axial portion 136 and the spacing portion 134 from the inlet port 140 to an area adjacent to the first end diffuser 170 to facilitate fluid communication between the inlet port 140 and the first interior space 176. The outlet channel 191 may extend through the axial portion 136 and the spacing portion 134 from the outlet port 142 to the transfer tube 174 to facilitate fluid communication between the outlet port 142 and the second interior space 178. To separate the inlet channel 190 and the outlet channel 191, the interface assembly 126 may include an axial portion divider wall 192 and a spacing portion divider wall 193. The axial portion divider wall 192 may be disposed within the axial portion 136 of the interface assembly 126 and extend longitudinally along the axial portion 136 (e.g., in a direction generally parallel with the housing axis 138), such that the inlet channel 190 is positioned on a first side of the axial portion divider wall 192 and the outlet channel 191 is positioned on a second side of the axial portion divider wall 192 that is opposite the first side. The spacing portion divider wall 193 may be disposed within the spacing portion 134 of the interface assembly 126 and extend longitudinally along the spacing portion 134 (e.g., in a direction generally perpendicular to the housing axis 138), such that the inlet channel 190 is positioned on a first side of the spacing portion divider wall 193 and the outlet channel 191 is positioned on a second side of the spacing portion divider wall 193 that is opposite the first side. Separating the inlet channel 190 and the outlet channel 191 enables pressurized air to flow into the impermeable housing 124 through the inlet channel 190 while product gas flows out of the impermeable housing 124 through the outlet channel 191.

In some embodiments, the interface assembly 126 may include a first portion 194 that is connected to, or formed integrally with, the base portion 164 of the impermeable housing 124, a second portion 196 that is connectable to the first portion 194, and a gasket 198 disposed between the first portion 194 and the second portion 196. The first portion 194 may be referred to as a first interface part and the second portion 196 may be referred to as a second interface part. In some embodiments, the axial portion 136 of the interface assembly 126 may be comprised primarily of the first portion 194. Furthermore, the first portion 194, the second portion 196, and the gasket 198 may cooperatively define the inlet channel 190 and the outlet channel 191. In such an embodiment, the first portion 194 may include the axial portion divider wall 192 to separate the inlet channel 190 and the outlet channel 191 along the axial portion 136. Furthermore, the gasket 198 may form the spacing portion divider wall 193 to separate the inlet channel 190 and the outlet channel 191 along the spacing portion 134. The gasket 198 may include gasket apertures 200 through which the outlet channel 191 may extend while maintaining separation between the inlet channel 190 and the outlet channel 191. The interface assembly 126 may be pneumatically connected to the transfer tube 174 using a coupling 202 to provide fluid communication between the outlet channel 191 and the second interior space 178.

The first portion 194 of the interface assembly 126 may include features 204 on which the gasket 198 may be supported. In some embodiments, the features 204 may extend through the gasket apertures 200 to further support the gasket 198 on the first portion 194 of the interface assembly 126 (as shown in FIGS. 3 and 4). Additionally or alternatively, the second portion 196 of the interface assembly 126 may include protrusions (not pictured) that extend toward the first portion 194 of the interface assembly 126 that are operable to urge the gasket 198 toward the first portion 194.

The gasket 198 may have any geometry and may be comprised of any material that, in combination, are sufficient to separate the inlet channel 190 and the outlet channel 191 during the PSA cycle (i.e., to prevent gas from traveling between the inlet channel 190 and the outlet channel 191). However, in some embodiments, the sieve modules 100 and the oxygen concentrator 102 may be configured such that during the PSA cycle, gas may travel through the inlet channel 190 at a pressure that is the same as a pressure with which gas travels through the outlet channel 191. Therefore, forces acting upon the gasket 198 resulting from different pressures existing on either side of the gasket 198 may be minimal, and thus may enable the gasket 198 to have a geometry that is relatively thin.

The second portion 196 of the interface assembly 126 may be connectable to the first portion 194 by any conventional means that are sufficient to maintain a sealing connection between the first portion 194 and the second portion 196. In some embodiments, the second portion 196 may be fixedly connected to the first portion 194 by, for example, welding, gluing, or the like. In other embodiments, the second portion 196 may be removably connected to the first portion 194 by, for example, clips, fasteners, or the like. In embodiments where the second portion 196 is removably connected to the first portion 194, a seal (not pictured) may be positioned at an interface between the first portion 194 and the second portion 196 to prevent gas from escaping from the inlet channel 190 or the outlet channel 191 during the PSA cycle. Furthermore, the first portion 194 and the second portion 196 may include opposing flanges that facilitate the connection between the first portion 194 and the second portion 196 (as shown in FIGS. 3 and 4).

Figure 5:
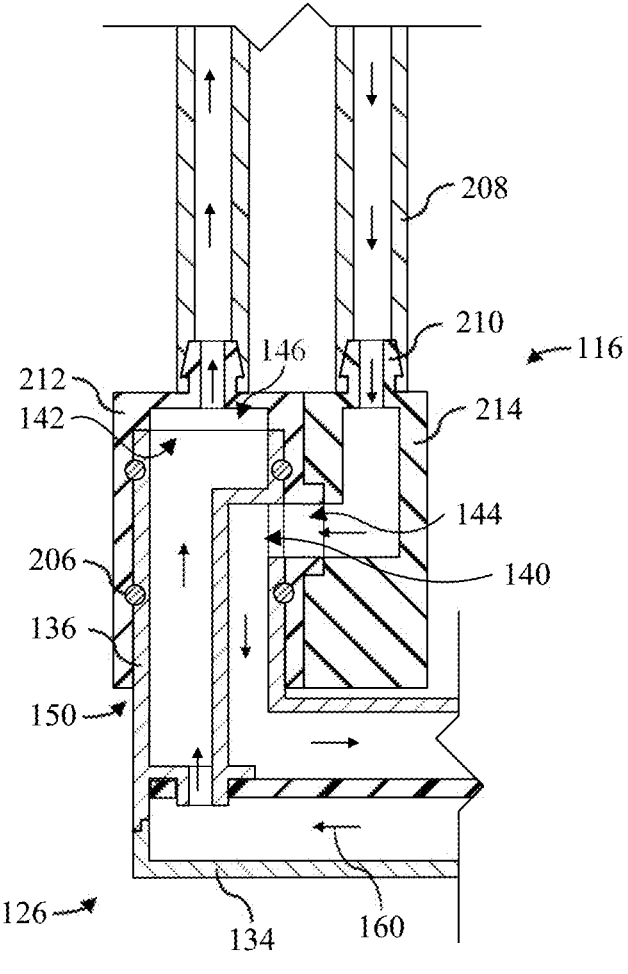
FIG. 5 is a partial cross-sectional, schematic view illustration showing an interface between the interface assembly and a manifold assembly of the oxygen concentrator.

FIG. 5 is a partial cross-sectional, schematic view illustration showing an interface between the interface assembly 126 and the manifold assembly 116 of the oxygen concentrator 102, wherein the arrows 160 represent a path in which gas may travel during the adsorption phase of the PSA cycle. During the purge phase of the PSA cycle, gas may travel in a direction that is opposite the direction of the arrows 160.

In some embodiments, the interface assembly 126 may include a plurality of interface seals 206 (e.g., two or more of the interface seals 206) positioned along the axial portion 136 of the interface assembly 126. In such an embodiment, the interface seals 206 may extend circumferentially around the axial portion 136 (e.g., may be an O-ring). In other embodiments, the interface seals 206 may be some other type of seal. The interface seals 206 may be operable to pneumatically connect the interface assembly 126 to the manifold assembly 116 by forming an airtight seal between the axial portion 136 of the interface assembly 126 and the interface cavity 150 when the sieve module 100 is in the fully inserted position. Furthermore, in some embodiments, the interface seals 206 may be configured to form separate pneumatic connections between the inlet port 140 of the interface assembly 126 and the manifold inlet 144 of the manifold assembly 116 and between the outlet port 142 of the interface assembly 126 and the manifold outlet 146 of the manifold assembly 116 (as shown in FIG. 5).

In the illustrated implementation, a first of the interface seals 206 in the form of an O-ring is positioned along the axial portion 136 between the inlet port 140 and the outlet port 142, such that the first of the interface seals 206 is positioned on a side of the inlet port 140 proximal the outlet port 142 (i.e., positioned proximal the outlet port 142 relative to the inlet port 140 in the longitudinal direction). Additionally, a second of the interface seals 206 in the form of an O-ring is positioned along the axial portion 136 between the inlet port 140 and the end of the axial portion 136 that is connected to the spacing portion 134, such that the second of the interface seals 206 is positioned on a side of the inlet port 140 distal from the outlet port 142 (i.e., positioned distal from the outlet port 142 relative to the inlet port 140 in the longitudinal direction). Positioning the first and the second of the interface seals 206 in such a configuration enables a pneumatic connection to be formed between the inlet port 140 and the manifold inlet 144 that is defined between the first and the second of the interface seals 206 when the axial portion 136 is fully inserted into the interface cavity 150. Such a configuration also enables a separate pneumatic connection to be formed between the outlet port 142 and the manifold outlet 146 that is defined by the first of the interface seals 206 when the axial portion 136 is fully inserted into the interface cavity 150. Therefore, when the axial portion 136 is fully inserted into the interface cavity 150, pressurized air may flow from the manifold inlet 144 to the inlet port 140 while product gas flows from the outlet port 142 to the manifold outlet 146.

In embodiments including the interface seals 206, the side wall 189 of the axial portion 136 may include features operable to prevent the interface seals 206 from moving along the axial portion 136 when the axial portion 136 is inserted into the interface cavities 150. For example, the side wall 189 may include divots configured to receive the interface seals 206 (e.g., divots extending circumferentially around the axial portion 136 into which an O-ring may be partially disposed). As another example, the side wall 189 may include ribs configured to support the interface seals 206 (e.g., ribs extending circumferentially around the axial portion 136 against which an O-ring may be positioned).

The manifold assembly 116 may be operable to facilitate fluid communication between the interface assembly 126 and the oxygen concentrator 102 through tubes 208, wherein the tubes 208 are operable to transfer gas between the manifold assembly 116 and the valve assembly 108. In some embodiments, the manifold assembly 116 may be configured to facilitate fluid communication between the interface assembly 126 of multiple of the sieve modules 100 and the oxygen concentrator 102. In such an embodiment, the manifold assembly 116 may extend between the interface cavities 150 that are provided for each of the sieve modules 100, such that the manifold assembly 116 is positioned adjacent to (or in some embodiments, defines or partially defines) each of the interface cavities 150.

In other embodiments, the manifold assembly 116 may be configured to facilitate fluid communication between the interface assembly 126 of only one of the sieve modules 100. In such an embodiment, the manifold assembly 116 may be positioned adjacent to (or may define or partially define) one of the interface cavities 150 corresponding to one of the sieve modules 100 (as shown in FIG. 5). Another of the manifold assembly 116 may be positioned adjacent to (or may define or partially define) another of the interface cavities 150 corresponding to another of the sieve modules 100.

The manifold assembly 116 may include attachment features 210 that pneumatically connect the manifold assembly 116 to tubes 208. In some embodiments, for example, the attachment features 210 may be tube fittings (as shown in FIG. 5). Although the two of the attachment features 210 shown in FIG. 5 are depicted as having similar geometries and sizes, the attachment features 210 may not be similar and may instead have different geometries and/or sizes.

In some embodiments, the manifold assembly 116 may include one of the attachment features 210 for each of the manifold inlet 144 and the manifold outlet 146 (as shown in FIG. 5). In such an embodiment, during the adsorption phase of the PSA cycle pressurized air may be delivered to the inlet port 140 through one of the tubes 208, and during the purge phase of the PSA cycle waste gas may be expelled out of the inlet port 140 into the same one of the tubes 208. In other embodiments, the manifold assembly 116 may include one of the attachment features 210 for the manifold outlet 146 and may include multiple (e.g., two) ones of the attachment features 210 for the manifold inlet 144. In such an embodiment, during the adsorption phase of the PSA cycle pressurized air may be delivered to the inlet port 140 through one of the tubes 208, and during the purge phase of the PSA cycle waste gas may be expelled out of the inlet port 140 into a different one of the tubes 208 (not shown).

Furthermore, the manifold assembly 116 may be comprised of a unitary body or may be comprised of a plurality of interconnected components. In an embodiment where the manifold assembly 116 is comprised of a plurality of interconnected components, for example, the manifold assembly 116 may include an outlet portion 212 and an inlet portion 214 (as shown in FIG. 5). The outlet portion 212 may be configured to facilitate fluid communication between the outlet port 142 and one of the tubes 208, and the inlet portion 214 may be configured to facilitate fluid communication between the inlet port 140 and another one (or other multiple) of the tubes 208. The outlet portion 212 may be connected to the inlet portion 214 in any suitable manner. For example, the outlet portion 212 may be glued or welded to the inlet portion 214 to form a fixed connection. As another example, the outlet portion 212 may be snapped, clipped, or fastened to the inlet portion 214 to form a removable connection.

FIG. 6 is a flowchart that shows a process 216 for replacing the sieve modules 100 inserted into the oxygen concentrator 102. One embodiment of the process 216 may include removing the door 152 from the housing 104 of the oxygen concentrator 102 to expose the first end 128 of the sieve modules 100. The process 216 may further include removing the interface assembly 126 of the sieve modules 100 from the interface cavities 150 by pulling on the first end 128 of the sieve modules 100 in an axial direction. The term "axial direction" as used herein refers to a direction generally along the housing axis 138. The process 216 may further include sliding the impermeable housing 124 of the sieve modules 100 out of the housing cavities 148 by continuing to pull on the first end 128 of the sieve modules 100 in the axial direction. The process 216 may further include replacing or restoring the sieve modules 100 to form new versions of the sieve modules 100. The process 216 may further include sliding the impermeable housing 124 of the new versions of the sieve modules 100 into the housing cavities 148 by pushing on the first end 128 of the new version of the sieve modules 100 in the axial direction. The process 216 may further include inserting the interface assembly 126 of the new versions of the sieve modules 100 into the interface cavities 150 by continuing to push on the first end 128 of the new versions of the sieve modules 100 in the axial direction. The process 216 may further include connecting the door 152 to the housing 104 of the oxygen concentrator 102 to cover the first end 128 of the new versions of the sieve modules 100.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A sieve module, comprising:
an impermeable housing including a first end, a second end opposite the first end, and a diffuser positioned at the second end that defines a first interior space and a second interior space within the impermeable housing, wherein the first interior space and the second interior space are in fluid communication solely at the second end of the impermeable housing;
an interface assembly connected to the first end of the impermeable housing, the interface assembly comprising:
an axial portion that is located radially outward from the impermeable housing and extends parallel to a housing axis of the impermeable housing,
an inlet port that is located on the axial portion and is in fluid communication with the first interior space of the impermeable housing, and
an outlet port that is located on the axial portion and is in fluid communication with the second interior space of the impermeable housing; and
an adsorptive material that is disposed within the first interior space of the impermeable housing for fluid communication with the inlet port and the outlet port.

2. The sieve module of claim 1, wherein the interface assembly further comprises:

a spacing portion pneumatically connected to the first end of the impermeable housing and extending from the impermeable housing to the axial portion.

3. The sieve module of claim 2, wherein:
the interface assembly further comprises a gasket disposed within the spacing portion of the interface assembly; and
the gasket defines at least part of an inlet channel that pneumatically connects the inlet port to the first interior space of the impermeable housing and an outlet channel that pneumatically connects the outlet port to the second interior space of the impermeable housing.

4. The sieve module of claim 2, wherein:
the interface assembly further comprises a first seal disposed along the axial portion, and a second seal disposed along the axial portion and spaced from the first seal,
the inlet port is disposed between the first seal and the second seal, and
the outlet port is disposed at an end of the axial portion that is distal from the spacing portion.

5. The sieve module of claim 4, wherein the first seal and the second seal extend circumferentially around the axial portion of the interface assembly.

6. The sieve module of claim 2, wherein:
the outlet port is disposed at an end of the axial portion that is distal from the spacing portion, and
the inlet port extends through a side wall of the axial portion.

7. The sieve module of claim 2, wherein the outlet port has an orientation that is in alignment with a housing axis of the impermeable housing and the inlet port has an orientation that is substantially perpendicular to the outlet port.

8. The sieve module of claim 1, wherein the adsorptive material is configured to filter nitrogen from gas traveling through the adsorptive material.

9. The sieve module of claim 8, wherein the adsorptive material comprises zeolite.

10. A sieve module, comprising:
an impermeable housing that extends along a housing axis;
a spacing portion connected to the impermeable housing of the sieve module such that the spacing portion extends away from the housing axis of the impermeable housing;
an axial portion that is connected to the spacing portion, is located radially outward from the impermeable housing, and extends away from the spacing portion in a direction parallel to the housing axis of the impermeable housing;
an inlet port positioned on the axial portion; and
an outlet port positioned on the axial portion.

11. The sieve module of claim 10, wherein the spacing portion is configured to be connected to the impermeable housing at a first end of the impermeable housing, and the axial portion is configured to extend from the spacing portion toward a second end of the impermeable housing.

12. The sieve module of claim 10, wherein:
the outlet port is disposed at an end of the axial portion that is distal from the spacing portion, and
the inlet port extends through a side wall of the axial portion.

13. The sieve module of claim 10, wherein the outlet port has an orientation that is parallel to housing axis of the impermeable housing and the inlet port has an orientation that is substantially perpendicular to the outlet port.

14. The sieve module of claim 10, further comprising:

an inlet channel extending from the inlet port through the axial portion and the spacing portion for fluid communication with the impermeable housing; and an outlet channel extending from the outlet port through the axial portion and the spacing portion for fluid communication with the impermeable housing.

15. The sieve module of claim 14, further comprising:

a gasket disposed within the spacing portion and configured to separate the inlet channel from the outlet channel in the spacing portion.

16. The sieve module of claim 14, wherein the axial portion includes a divider wall to separate the inlet channel from the outlet channel in the axial portion.

17. An interface assembly for a sieve module, comprising:

a first interface part;

a second interface part that is connected to the first interface part; and a gasket disposed between the first interface part and the second interface part to define at least part of an inlet channel and an outlet channel, wherein the inlet channel and the outlet channel are separated by the gasket, wherein the first interface part and the second interface part cooperate to define a spacing portion that extends in a first direction, and the first interface part defines an axial portion that is connected to the spacing portion and extends away from the spacing portion in a second direction.

18. The of claim 17, wherein:

an inlet port is positioned on the axial portion and is in communication with the inlet channel, and an outlet port is positioned on the axial portion and is in communication with the outlet channel.

19. The of claim 17, wherein the second direction is perpendicular to the first direction.

20. The of claim 17, wherein the axial portion includes a divider wall to separate the inlet channel from the outlet channel in the axial portion.

* * * * *